US008211906B1

(12) United States Patent
Scherrer

(10) Patent No.: US 8,211,906 B1
(45) Date of Patent: Jul. 3, 2012

(54) METHOD OF INHIBITING GROWTH OF NEOPLASTIC CELLS AND INHIBITING INFECTION BY ADMINISTERING AN IMMUNE ENHANCER DRUG

(76) Inventor: Lawrence C. Scherrer, Eau Claire, WI (US)

( * ) Notice: Subject to any disclaimer, the term of this patent is extended or adjusted under 35 U.S.C. 154(b) by 1083 days.

(21) Appl. No.: 10/912,009

(22) Filed: Aug. 4, 2004

Related U.S. Application Data

(60) Provisional application No. 60/492,681, filed on Aug. 5, 2003.

(51) Int. Cl.
*A01N 43/42* (2006.01)
*A01N 43/52* (2006.01)

(52) U.S. Cl. .................. 514/290; 514/393

(58) Field of Classification Search .............. None
See application file for complete search history.

(56) References Cited

U.S. PATENT DOCUMENTS

| | | | |
|---|---|---|---|
| 4,689,338 A | 8/1987 | Gerster | |
| 5,028,422 A * | 7/1991 | Tanner et al. | 424/85.4 |
| 5,238,944 A | 8/1993 | Wick et al. | |
| 5,939,090 A | 8/1999 | Beaurline et al. | |
| 6,200,592 B1 | 3/2001 | Tomai et al. | |
| 2003/0091540 A1* | 5/2003 | Ahmad et al. | 424/93.3 |
| 2003/0199538 A1 | 10/2003 | Skwierczynski | |
| 2004/0265351 A1 | 12/2004 | Miller et al. | |

OTHER PUBLICATIONS

Geisse et al. "Imiquimod 5% cream for the treatment of superficial basal cell carcinoma: a doublel-blind, randomized, vehicle-controlled study." J. Am. Acad. Dermatol 2002; 7: 390-398. 9 sheets.*
Marks et al. "Imiquimod 5% cream in the treatment, of basal cell carcinoma: Results of a multicenter 6-week-dose-response trial" J. Am. Dermatol. 2001; 807-813. 7 sheets.*
Beutner et al. "Therapeutic resposne of basal cell carcinoma to the immune response modifier imiquimod 5% cream" J. Am. Dermatol. 1999; 41: 1002-1007. 6 sheets.*
Schacker, Timothy W. "Imiquimod 5% cream does not alter the natural history of recurrent herpes genitalis: a phase II, randomized, double blind, placebo controlled study." Antimicrobial Agents and Chemotherapy. Oct. 2002, p. 3243-3248. 6 sheets.*
Minsue, T et al. "Treatment of a Large Superfiical Basal Cell Carcinoma with 5% Imiquimod: A case report and review of the literature." 2002. Dermatol. Surg. 2002; 28: 344-346. 3 sheets.*
Stockfleth et al. "The use of Toll-like receptor-7 agonist in the treatment of basal cell carcinoma: an overview." British Journal of Dermatology, 149 (SUppl. 66), 53-56. 4 sheets.*
Hurd et al. "Practical uses of the interferons in dermatology." International Journal of Dermatology. 1998, 37, 881-816. 16 sheets.*
Johnson et al. "Relationships between drug activity in NCI preclinical in vitro and in vivo models and early clinical trials" British Journal of Cancer (2001). 84(10). 1424-1431. 8 sheets.*
Sausville et al. "Contributions of Human Tumor Xenografts to Anticancer Drug Development" Cancer Research 2006; 66:7. 4 sheets.*
Clark et al. "Adjuvant High-Dose Bolus Interleukin-2 for Patients with High-Risk Renal Cell Carcinoma: A Cytokine Working Group Randomized Trial." Journal of Clinical Oncology, vol. 21, No. 16. 2003. pp. 3133-3140.*
Sauder, "Immunomodulatory and pharmacologic properties of imiquimod." J. Am. Acad. Dermatol. Jul. 2000.*
"Principles of Cancer Therapy." Cecil's Textbook of Medicine (Twenty-First Edition). W.B. Saunders Company. 2000. pp. 1060-1074.*
Baxter Pharmaceuticals. Potassium Chloride in Sodium Chloride (0.9%) Intravenous Infusion BP. 2000.*
Lieberman et al. Pharmaceutical Dosage Forms: Disperse Systems. vol. 2. 1998.*
Reiter et al. Cytokine induction in mice by the immunomodulator imiquimod. J. Leuko. Biol. 1994.*
Medline Plus. Basal Cell Carcinoma. Web Resource [hhtp://www.nlm.nih.gov/medlineplus/ency/article/00824.htm]. 2008.*
National Cancer Institute. Definition of intralesional. Web Resource [http://nci.nih.gov/dictionary/?CdrID=44684. 2010.*
Urosevic et al. Immunotherapy for nonmelanoma skin cancer. Cancer, Jan. 15, 2002; vol. 94, No. 2.*
Leuner et al. Improving drug solubility for oral delivery using solid dispersions. European Journal of Pharmaceutics and Biopharmaceutics, 50, 2000, 47-60.*
Sterry et al. Imiquimod 5% cream for the treatment of superficial and nodular basal cell carcinoma: randomized studies comparing low-frequency dosing with and without occlusion. British Journal of Dermatology, 2002, 147: 1227-1236.*
Chollet, JL, et al. "Development of Topically Active Imiquimod Formulation," Pharmacology Developmental Technology, 1999, 4(1):35-43.
Gibson, SJ, et al. "Plasmacytoid Dendritic Cells Produce Cytokines and Mature in Response to the TLF7 Agonists, Imiquimod and Resiquimod," Cellular Immunology, 2002, 218:74-86.
Sidky, et al. "Inhibition of Murine Tumor Growth by an Interferon-Inducing Imidazoquilolinamine," Cancer Research, 1992, 52:3528-33.
Stephenson, Joan. "New Therapy Promising for Genital Herpes," Journal American Medical Association, 2001, 285, 17.
Suzuki, H, et al. "Imiquimod, A Topical Immune Response Modifier, Induces Migration of Langerhans Cells," J. Investigative Dermatology, 2000, 114:135-41.
Tomai, Ma, et al. "The Immune Response Modifiers Imiquimod and R-848 Are Potent Activators of B Lymphocytes," Cellular Immunology, 2000, 203:55-65.
Kim KH, et al. "Intralesional Interferon A-2B in the Treatment of Basal Cell Carcinoma and Squamous Cell Carcinoma: Revisited," Derm. Surg. 2004 30(1):116.

* cited by examiner

*Primary Examiner* — Brandon Fetterolf
*Assistant Examiner* — Anna Pagonakis
(74) *Attorney, Agent, or Firm* — DeWitt, Ross & Stevens S.C.; Charles S. Sara; Daniel A. Blasiole

(57) ABSTRACT

Disclosed is a method of inhibiting the growth of neoplastic tumors and lesions and localized infections by administering an Immune Response Modifier (IRM) drug to human patients suffering from such tumors, lesions or infections. IRMs act by stimulating cellular immunity and have been found to have both anti-viral and anti-tumor effects. By administering IRM drugs directly into a tumor, lesion or infection, the cells of the tumor, lesion or infection, as well as those surrounding the tumor, lesion or infection can be stimulated to increase their cellular response, thereby inhibiting the growth of such tumors, lesions or infections.

13 Claims, No Drawings

METHOD OF INHIBITING GROWTH OF NEOPLASTIC CELLS AND INHIBITING INFECTION BY ADMINISTERING AN IMMUNE ENHANCER DRUG

CROSS-REFERENCE TO RELATED APPLICATIONS

This application claims priority under 35 USC §119(e) to U.S. Provisional Application Ser. No. 60/492,681, filed 5 Aug. 2003, the entirety of which is incorporated herein.

REFERENCE TO CITATIONS

Complete bibliographical citations to the references can be found in the Bibliography preceding the Claims.

FIELD OF THE INVENTION

The present invention relates generally to a method of treating neoplastic tumors or lesions and localized infections through the internal administration of Immune Response Modifer (IRM) drugs. More specifically, the invention is directed to a method of inhibiting the growth of neoplastic tumors or lesions and localized infections, the method comprising administering imidazoquinolinamines to human patients having such tumors, lesions or infections.

DESCRIPTION OF THE PRIOR ART

Many classical treatments for diseases rely on providing the body with drugs or compounds that actively fight the disease-causing agents. Antibiotics are a good example because while there are many different classes of antibiotics, all work by interfering with a bacteria's ability to reproduce. Such interference limits the infection and allows the body's own defenses to overcome the infection. However, some diseases such as viral diseases or neoplastic diseases do not respond to antibiotics. Further, many bacteria are becoming antibiotic resistant, requiring new classes of drugs that aid in fighting diseases. One such class of drugs is called "Immune Response Modifier" (IRM) drugs.

Immune response modifier drugs were first identified in the 1980s with the isolation of imiquimod, 1-(2-methylpropyl)-1H-imidazo[4,5-c]quinolin-4-amine. Imiquimod is just one example of a drug which falls into a larger class of drugs referred to herein as non-nucleoside imidazoquinolinamines. Although studies using cell culture systems show no direct anti-viral or anti-tumor effect of IRM drugs, in-vivo studies have revealed a broad range of immune activities. The mechanism of action of IRM drugs is not completely understood, but they all appear to stimulate the immune system, thereby enabling it to overcome certain infections.

Current research indicates that IRMs activate the immune system by binding to toll-like receptors, which causes induction of cytokines. Some IRMs include: alpha- and beta-interferon (INF); interleukins 1, 6, 8, 10, and 12, and alpha-tumor necrosis factor, and other forms of tumor necrosis factor (TNF). In addition, IRMs also increase the activation of Langerhans cells, the major antigen-presenting cells within the epidermis. Therefore, while in vitro studies show that the IRMs do not have a direct antiviral effect, in vivo studies show that the IRMs do have an indirect antiviral effect by causing the increases in the immune responses indicated above.

While IRM drugs as a class are relatively new, one IRM drug, imiquimod, is currently approved for topical use in the United States. For instance, the genital herpes medicinal cream Aldara®, used for the topical treatment of external genital and perianal warts in adult patients, uses 5% imiquimod as the active substance. Typical protocols require Aldara® to be applied three times per week and should remain on the skin for 6-10 hours until the warts or lesions have disappeared for at least 16 weeks.

Imiquimod is a heterocylic amine. It is a white to off-white crystalline solid. A hygroscopic compound, imiquimod is almost insoluble in water and common organic solvents in the free base form, although it is more soluble as a hydrochloride salt. A relatively stable compound, imiquimod does not possess any asymmetric carbon atoms and exhibits no stereoisomerism. Imiquimod is synthesized in a six-step process. Crude imiquimod is purified by converting it to an imiquimod salt which is treated with activated carbon, filtered, basified to precipitate the active form of imiquimod, washed with a solvent and dried in a vacuum. Individual impurities typically do not exceed 0.1%, with total impurities totaling not more than 0.3%.

In vitro studies of imiquimod show that imiquimod induces cytokine secretion in a wide variety of cell types including spleen, bone marrow, liver, peritoneal exudates and alveolar macrophages. While the cytokines produced differ between cell types, all produce results consistent with a cell surface receptor for imiquimod. Cytokine induction typically occurs 1-2 hours after exposure and generally peaks after 8 hours. In vivo studies confirm imiquimod's ability to stimulate cytokine production in mice, rats, guinea pigs and monkeys.

Further, the antiviral activity of imiquimod has been examined in cell cultures and in in vivo animal infection models. In vitro imiquimod causes a 50% plaque reduction in cells infected with viruses such as rhinovirus 1A, respiratory syncytial virus and varicella zoster. In guinea pigs, imiquimod effectively treats infections of primary genital herpes with a single dose. In monkeys, imiquimod is effective against the Rift Valley Fever and Banzi viruses. Further, imiquimod has been shown to be an effective anti-tumor agent in mice implanted with a number of different tumor cell types.

The pharmocokinetic profile of imiquimod shows imiquimod is rapidly absorbed following oral administration and that systemic exposure to imiquimod is minimal after dermal administration. Similarly, distribution studies using a radiolabeled compound administered orally showed higher levels of imiquimod in the organs of elimination as compared to the plasma after 72 hours. This indicates that imiquimod is actively excreted and not reabsorbed in the kidney.

The solubility of the weakly basic imiquimod in aqueous solution is very limited, but the hydrochloride salt is soluble at concentrations up to 10 mg/ml (1%) [Vogel, et al]. In a recent study, imiquimod hydrochloride solution was injected subcutaneously in mice to give a systemic effect [Bernstein, et al]. In this study, imiquimod enhanced the activity of a vaccine against herpes simplex virus. Additionally, it has been demonstrated that topical imiquimod enhanced contact allergy to dinitrochlorobenzene [Suzuki, et al].

Imiquimod is currently approved for topical use against genital and perianal warts. However, imiquimod is also being studied for its effects against a variety of other dermatological conditions, such as non-genital warts, molluscum contagiousm, basal cell carcinoma, Bowens disease, solar keratoses, cervical cancer, and herpes simplex. Topical administration of imiquimod is predicated on its incorporation into a topical vehicle such as, for example, an ointment or its current delivery via a 5% cream.

Imiquimod is described in U.S. Pat. No. 4,689,338 (the '338 patent) to Gerster. The '338 patent describes a new class of molecule called an "immune response modifier (IRM)."

IRMs are the subject of three other U.S. Pat. Nos. 5,238,944 to Wick et al. (the '944 patent); 5,939,090, to Beaurline et al. (the '090 patent); and 6,200,592 to Tomai et al (the '592 patent), all incorporated herein by reference for their description of the synthesis and effects of imidazoquinolinamines.

The '338 patent to Gerster describes a large class of the 1H-imidazo[4,5-C]quinolin-4-amine compounds and teaches methods for producing the compounds. Further, the '338 patent specifically teaches topical application of the IRM, e.g., intravaginally or on the skin. However, while a large number of examples are included in the '338 patent, only two of them discuss uses of the IRM compounds. Example 198 describes an intravaginal application of the cream to guinea pigs and the effect on interferon activity. Example 199 describes the intravenous and intravaginal application of the compounds to three monkeys in each group. Serum from the monkeys was then drawn and incubated with human fibroblast cells. The fibroblast cells were later challenged with mengovirus to assay whether the serum protected the cells. The results suggest that imiquimod induces interferon when administered intravaginally.

U.S. Pat. No. 5,238,944 to Wick et al. describes other formulations for topical treatment using the compounds described in the '338 patent (in particular 1H-imidazo[4,5-C]quinolin-4-amine, imiquimod). In particular the '338 patent describes the use of adhesive-coated sheets for the topical or transdermal delivery of imiquimod to treat viral infections.

U.S. Pat. No. 5,939,090 to Beaurline et al. describes a gel formulation for topical drug delivery of the compounds. In fact, the abstract describes the effects of the drug as that "which when applied topically induce cytokines." In particular, the patent describes the use of propylene glycol in the ointment because it thickens the gel formation such that the gel is maintained at body temperature.

U.S. Pat. No. 6,200,592 to Tomai et al. describes the use of the immune response modifier compounds for the treatment of TH2 (T helper-type 2) mediated diseases. The effect is to inhibit the production of interleukins 4 and 5 and suppress eosinophilia. Examples of TH2 processes include atopic dermatitis, asthma, allergic rhinitis, and the immune response to certain fungal and parasitic infections. The method for administering the IRM compounds is described as parenterally, transdermally, and orally.

Other IRM compounds are also currently being studied. For instance, resiquimod is being evaluated as a topical gel treatment for genital herpes with great success. A 2001 study found that one episodic treatment of resiquimod not only eradicates genital herpes lesions but also seems to act like a vaccination in prolonging the time to the next recurrence [Stephenson]. The exact mechanism of action remains unclear.

While the patents described above describe a number of methods available for the delivery of imiquimod, they remain inadequate in many ways. For instance, topical administration of imiquimod creams results in significant skin irritation. Further, topical treatments must be applied repeatedly and are unable to deliver the IRM to lesions located deeper within the skin. Oral administration of IRMs is also problematic. While oral administration of imiquimod can deliver the IRM internally to lesions located deep within the skin, it causes significant systemic toxicity to the patient. This toxicity limits the effectiveness of the drug when delivered orally.

Therefore, a long-felt and unmet need exists for a method of delivering an IRM compound, such as imiquimod, to a lesion, tumor or localized infection, thereby eliminating the local irritation and poor penetration of topical delivery, while simultaneously avoiding the systemic toxicity of oral delivery.

SUMMARY OF THE INVENTION

The physical and chemical properties of imiquimod make it an ideal candidate for intralesional or intratumoral delivery. All of the limitations noted above can be avoided by an intralesional or intratumoral administration of a suspension of imiquimod or other IRM compound directly into the targeted area. Its low solubility in water and organic solvents allows it to dissolve slowly in the body, creating a sustained immune response reaction. This slow dissolution of imiquimod would also avoid the systemic toxicity common to oral delivery methods of imiquimod.

An objective of the present invention is to use intralesional delivery of Immune Response Modifier (IRM) compounds such as imiquimod to induce immuno-stimulatory effects to take advantage of their therapeutic effects. IRMs have potent anti-viral and anti-tumor effects. By harnessing these effects to increase the innate immune response in fighting disease agents at a cellular level, a new treatment for internal neoplastic lesions and tumors as well as localized infections may be as effective as other forms of treatment which have much greater systemic side effects.

A further objective of the present invention is to take advantage of the physical and chemical properties of IRM compounds such as imiquimod to produce a novel intralesional delivery of an IRM as a particulate suspension. For example, the poor solubility of IRM compounds has made past attempts at topical delivery using creams or ointments problematic. However, the low solubility of IRMs is beneficial in an intralesional delivery method. Using an intralesional delivery of the IRM, a single dose of imiquimod, or other IRM with similar properties, could provide sustained, localized immune stimulation without the problematic skin irritation and limited or no systemic toxicity. This represents a significant advantage over conventional topical delivery, which in the case of basal cell cancers, current protocols require topical application once daily for 5-7 days per week for 4-12 weeks.

In the preferred version of the invention, a novel method of treating cancer is disclosed comprising administering an IRM drug intralesionally in a therapeutic dose. Intralesional delivery may improve treatment of certain cancers such as basal cell cancer. For example, it is known that the deeper portions of basal cells cancer tumors do not respond as well to the conventional topical delivery method of IRMs as superficial areas of the tumor. This has so far limited the use of IRMs to thin, "superficial" basal cell cancers. The present invention provides an IRM, such as imiquimod, in a particulate suspension that can be placed deeper in the lesion to also treat deeper, thicker tumors.

Other examples of cutaneous tumors treatable by this method include squamous cell carcinoma, actinic keratosis, melanoma, cutaneous T cell lymphoma, and Kaposi's sarcoma. These tumors have all been demonstrated to respond to topical imiquimod or systemic interferon.

Additionally, intralesional suspensions of IRMs such as imiquimod may be used to treat metastatic lesions of cutaneous tumors. Topical imiquimod has successfully treated cutaneous metastatic melanoma when used under occlusion [Wolf, et al], lending weight to the claim that intralesional delivery of imiquimod will also be effective. Further, tumors that respond well to systemic administration of interferon, such as renal cell carcinoma and head and neck cancers, could also respond to intralesional imiquimod. The invention will benefit any tumor where a localized enhanced immune response could be effective in limiting the growth of the cancer. Further, any site in the body accessible by needle or catheter could be treated with intralesional delivery imiquimod, making the present invention useful in all types of illnesses where a stimulated immune response will be beneficial. Any route of injection could be used to direct the IRM to the desired target, including intradermal, intratumoral, intralesional, intramuscular, intravascular or subcutaneous routes.

In another version of the invention, intralesional imiquimod suspension could be administered to treat viral infections such as warts, molluscum, herpes simplex or varicella-zoster virus. Further, any localized infection or infestation could be treated, including bacterial, fungal, protozoal or larval, where it is believed a localized immune response would be of benefit. Examples could include infections such as blastomycosis, sporotrichosis, mycetomas (fungal or bacterial) and leishmaniasis. Further, other skin lesions or tumors such a keloids, or hypertrophic scars, hemangiomas or tattoos may also be treated by the present invention.

In yet another version of the invention, intralesional delivery of IRMs such as imiquimod is used to enhance an immune response to a vaccine used to treat any infection or tumor. Intratumoral imiquimod may enhance the host response to a specific tumor treated with the suspension. Similarly, the invention could enhance the immune response when used as an adjuvant to any vaccine—whether that vaccine is being used to treat or prevent infection or tumor.

In another version of the invention, imiquimod powder is administered into the blood or lymphatic vascular system with the intent of causing the compound to collect in the desired area by the action of normal blood flow or lymphatic drainage. By this method a tumor can be embolized (i.e., particles trapped in tumor vasculature) with the drug. Suspensions administered into a lymphatic channel can collect in a lymph node of biological importance. In both of these examples the immune response would be boosted at the target site.

In a final version of the invention, a particulate suspension of imiquimod is administered through subcutaneous or intramuscular delivery in large quantities to provide continuous release of imiquimod. This will create a sustained physiologic serum level of the drug, causing systemic cytokine release. This could be used in situation where subcutaneous interferon injections are used such as in the adjuvant treatment of cancers such as melanoma and leukemia.

In summary, the present invention employs the advantageous effects of the non-nucleoside imidazoquinolinamines in directly modulating the cell-mediated immunity of components of cells in a diseased tumor or lesion. While in some cases the lesion may be a spontaneous cancer, in other cases the lesion may be virally induced. Other lesions may be localized infections, including both those with bacterial and viral origins. In addition, the poor solubility of the compounds described herein is a positive advantage to their intralesional administration. Because of their poor solubility, intralesional administration of small amounts of IRMs such as imiquimod results in sustained, localized stimulation of the immune response system. This avoids the adverse reactions resulting from topical or oral delivery of the IRM compounds.

The objects and advantages of the invention will appear more fully from the following detailed description of the preferred embodiment of the invention made in conjunction with the accompanying drawings.

DETAILED DESCRIPTION OF THE INVENTION

The invention comprises a treatment of an internal neoplastic disease or localized infection. More particularly, the invention comprises the intralesional administration of an immune response modifier drug directly into an internal lesion.

Neoplastic diseases are those that lead to the creation of any new or abnormal growth such as a tumor or lesion. Common neoplastic diseases include carcinomas, such as basal cell carcinoma and squamous cell carcinoma. While many individual neoplastic diseases are rare, as a group, neoplastic diseases afflict millions of people each year. The social, economic and health impact from neoplastic diseases is therefore far-reaching and extends beyond the victim to their family, employers, co-workers and friends. Therefore, providing an IRM drug that can effectively enhance the survival of one afflicted with a neoplastic disease such as sarcoma, basal cell cancers and more, will help millions of people.

Conventional treatment for such neoplastic diseases includes topical, locally applied creams containing imiquimod or oral administration of the imiquimod. Topical delivery often causes severe skin irritation, while oral delivery often causes severe, dose-limiting systemic toxicity, thought to be due to the systemic induction of interferon and other cytokines. Imiquimod has physical properties that make it difficult to use as a topical preparation. Further, imiquimod's biological properties make it difficult to use as a parenteral or oral agent (i.e., nausea, fever and other flu-like symptoms).

Intralesional suspensions are also commonly used forms of treatment. For instance, intralesional suspensions of triamcinolone have been injected into the desired location to provide localized anti-inflammatory activity in intra-articular injection in arthritis and intralesional injection of acne cysts and hypertrophic or keloidal scars. The poor solubility of the compound sustains the localized response and limits systemic toxicity. IRMs may also be useful in treating dermatologic conditions such as warts and molluscum.

Warts are non-cancerous skin growths caused by a viral infection in the top layer of the skin. Viruses that cause warts are called human papillomavirus (HPV). Warts are usually skin-colored and feel rough to the touch, but they can be dark, flat and smooth. The appearance of a wart depends on where it is growing. Warts are passed from person to person, sometimes indirectly. The time from the first contact to the time the warts have grown large enough to be seen is often several months. The risk of catching hand, foot, or flat warts from another person is small. Some people get warts depending on how often they are exposed to the virus. Wart viruses occur more easily if the skin has been damaged in some way, which explains the high frequency of warts in children who bite their nails or pick at hangnails. Some people are just more likely to catch the wart virus than are others, just as some people catch colds very easily. Patients with a weakened immune system also are more prone to a wart virus infection. IRMs can offer a novel treatment to inhibit the growth of such warts.

Molluscum is a common skin disease caused by a virus which affects the top layers of the skin. The virus develops growths that are easily spread by skin contact. Similar to warts, this virus belongs to the poxvirus family and enters the skin through small breaks of hair follicles. It does not affect any internal organs. The molluscum virus is transmitted from the skin of one person who has these growths to the skin of another person. It occurs most often in cases where skin-toskin contact is frequent, in young children, especially among siblings, or in swimming pools. If growths are present in the genital area, molluscum can be sexually transmitted. IRMs can offer a novel treatment to inhibit the growth of molluscum.

While the use of imiquimod as an injected suspension is not intuitive, careful analysis of the physical properties and biological activity of imiquimod shows it to be uniquely suited for use as an injected suspension. Detailed analysis of available data proves that particulate imiquimod in tissue will cause an immune response. There is evidence that intralesional delivery of an imiquimod suspension would provide the potent immune induction of locally available imiquimod without the damaging side effects. Further, an imiquimod suspension would be effective based on previous studies of intralesional cytokines to treat BCC. It has been shown that intratumoral/intralesional injection of cytokines such as IFN-alpha is effective for clearing tumor, but the short half-life of this agent typically necessitates multiple injections [Kim, et al]. It is therefore possible that intralesional imiquimod could provide a cure for small tumors with a single injection.

Imiquimod's poor solubility would seem to make it unsuitable as an injected drug. However, this seemingly unfavorable property makes imiquimod a perfect candidate for intralesional injection. Triamcinolone hexacetonide (Aristospan) provides a useful pharmacologic analogy. Aristospan is a glucocorticoid and is very poorly soluble in water (2 µg/ml, or 3.75 µM based on molecular weight of 532.7 g/mol). Because of this poor solubility it dissolves very slowly when it is injected into skin or joint spaces. This slow dissolution gives a pronounced localized effect without the systemic effect of a systemic glucocorticoid, such as prednisone. Imiquimod has physical properties very similar to triamcinolone hexacetonide. At physiologic pH, it is soluble to only 1-2 µg/ml (4 µM based on molecular weight of 240.3 g/mol for the free base) [Chollet, et al]. Assays in mouse and human cell systems show imiquimod is most active at exactly this concentration. Specifically, imiquimod induced proliferation of mouse spleen cell cultures with the maximum activity at 1 µg/ml [Tomai, et al] and it induced interferon-alpha production in isolated human mononuclear cells maximally at a concentration of 3 µM [Gibson, et al]. Therefore, intradermal or intralesional imiquimod clearly should dissolve enough to give a localized effect. However, given the limited solubility of imiquimod, systemic cytokine stimulation would be highly unlikely with small volume single-site injection.

Therefore, while the intralesional use of a particulate suspension of imiquimod has not been suggested before, it can provide the potent immune induction of locally available imiquimod without the damaging side effects. Using a similar method, any IRM could be administered into a neoplastic lesion or tumor or a localized infection as an aqueous suspension. The imiquimod or IRM would slowly dissolve by direct dissolution of the free base or by a slow equilibrium to the protonated form of the drug (e.g. the hydrochloride salt). The rate of dissolution could be modified by adjusting the size of the drug particle, adjusting the pH of the solution by use of acid, base or by use of a buffering solution.

Adjusting the particle size would likely alter the kinetics of imiquimod dissolution, thereby allowing the dissolution of the suspension to be more readily controlled. For instance, a very fine particle size would dissolve more quickly and give higher concentrations of active drug while larger particle sizes would dissolve more slowly to give a more sustained but more tightly localized biological response. Additionally, because the imiquimod particles can be either crystalline or amorphous in form, the form of the particulate can be adjusted to change the kinetics of the particulates dissolution in the body. Further, the rate of dissolution can be affected by the pH of the tissue the suspension is injected into. For instance, if a specific tumor or area of inflammation had a lower pH, as is common, the rate of dissolution of the imiquimod suspension could be enhanced. Any pharmacologic or physical intervention which lowers tissue pH would likely enhance the immune response stimulated by the imiquimod injection.

It has already been demonstrated that an imiquimod suspension can be made [Sidky, et al]. There, the authors made a suspension of a fine imiquimod powder in a 2% hydroxypropylcellulose solution for oral administration to mice by gavage. This adds weight to our conclusion that imiquimod will be a successful treatment in an intralesional injection of a particulate suspension. However, intralesional delivery was not suggested in the Sidky article.

For administration, a needle may be inserted into the affected site and a measured quantity of the suspension introduced or an intralesional catheter is placed directly into the affected site. The catheter may be connected to a pump, which thereby administers an appropriate dose at a directed time. In contrast, the catheter may be left indwelling without a pump and require manual administration of the drug.

Sterile imiquimod powder will be mixed with a sterile solution to form a particulate suspension. This suspension will be made in an appropriate solution such as saline (0.9% w/v NaCl). This solution may contain hydroxypropylcellulose, or other agents such as polyethylene glycol, polysorbate, surfactant or other additives required to maintain the suspension.

The suspension will be injected intradermally into mice or rats. At various time points after injection, skin biopsy will be performed. Tissue samples will be assayed for induction of interferon or other cytokines by ELISA or other appropriate method. This will demonstrate the ability of intradermal imiquimod to induce local production of cytokines as is seen with topical imiquimod. Serum will also be analyzed to evaluate the effect of intradermal imiquimod on systemic interferon or other cytokine levels. Alternatively, immunologic staining techniques or molecular techniques may be performed to demonstrate tissue production of interferon, TNF or other cytokines, or demonstrate induction of the mRNA of such cytokines.

Because IRMs act by increasing cellular immune responses, the current invention discloses a novel method to inhibit the growth of many localized diseases. For example, some virally induced diseases, such as molluscum, are localized to a specific organ. Similarly, some bacterial diseases, such as septic arthritis, are localized at internal sites.

In addition, intralesional administration of an IRM represents a therapeutically effective method of inhibiting the growth of various neoplastic diseases. Neoplastic diseases often result in tumors, whether spontaneous or virally induced, that are initially localized to a specific organ or tissue. In these non-systemic diseases, localized administration of an IRM such as imiquimod will act at the cellular level via cell mediated immunity to positively affect the course of the disease.

The present invention also discloses a method of enhancing the survival of a human patient when the activation of Langerhans cells is beneficial. Administration of an IRM such as imiquimod can act to activate Langerhans cells, which are a key component of the acquired immune system for presentation of antigens to T cells. Thus, while the effect of intralesional administration of imiquimod to patients suffering from localized diseases should greatly increase cellular defenses against those diseases, an increase in acquired immunity directed toward the localized antigens can also be expected.

Further, the current invention could be used to treat TH2 type diseases such as atopic dermatitis and asthma or autoimmune diseases that have been shown to have TH2 characteristics. Th2 cells activate B cells by producing a molecule called interleukin-4, which helps TH2 cells stay alive. The TH2 cell recapitulates its own existence by producing Interleukin-4, which acts to block T cell death by dismantling a specific"death" pathway that T cells activate in order to die. In a localized infection, TH2 processes may use interleukin-4 as a self-sustaining "survival factor" to perpetuate their own growth. The IRM compound of the present invention could block the ongoing survival of TH2 cells, which is induced by interleukin-4. Such a drug could be used temporarily during the peak of the infection, and would ideally preclude the whole inflammatory cascade before it begins. In such non-localized diseases, larger quantities of an IRM compound would be delivered to tissue (intradermal, subcutaneous, or intramuscular) in order to induce a systemic effect.

It is understood that the invention is not confined to the particular construction and arrangement of parts herein illustrated and described, but embraces such modified forms thereof as come within the scope of the following claims.

BIBLIOGRAPHY

1. Bernstein, D I, et al. "Adjuvant Effects of Imiquimod on Herpes Simplex Virus Type 2 Glycoprotein Vaccine in Guinea Pigs," J. Infectious Diseases, 1993, 167:731-5.
2. Chollet, J L, et al. "Development Of Topically Active Imiquimod Formulation," Pharmacology Developmental Technology, 1999, 4(1):35-43.
3. Gibson, S J, et al. "Plasmacytoid Dendritic Cells Produce Cytokines And Mature In Response To The TLF7 Agonists, Imiquimod And Resiquimod," Cellular Immunology, 2002, 218:74-86.
4. Sidky, et al. "Inhibition of Murine Tumor Growth by an Interferon-Inducing Imidazoquilolinamine," Cancer Research, 1992, 52:3528-33.
5. Stephenson, Joan. "New Therapy Promising for Genital Herpes," Journal American Medical Association, 2001, 285, 17.
6. Suzuki, H, et al. "Imiquimod, A Topical Immune Response Modifier, Induces Migration of Langerhans Cells," J. Investigative Dermatology, 2000, 114:135-41.
7. Tomai, M A, et al. "The Immune Response Modifiers Imiquimod And R-848 Are Potent Activators Of B Lymphocytes," Cellular Immunology, 2000, 203:55-65.
8. Vogel, F R, et al. "A Compendium of Vaccine Adjuvants and Excipients ($2^{nd}$ Edition)," National Institutes of Health website, http://vrc.nih.gov/daids/vaccine/pdf/compendium.pdf
9. Wolf, I H, et al. "Topical Imiquimod in the Treatment of Metastatic Melanoma to Skin," Archives of Dermatology, 2003, 139, 273-76.
10. Tyring, Stephen, et al. "Imiquimod: An International Update on Therapeutic Uses in Dermatology," Int'l J. of Dermatology, 2002, 41, 810-816.

What is claimed is:

1. A method of inhibiting growth of neoplastic tumors and lesions, the method comprising administering to a mammal in need thereof a therapeutically effective, growth-inhibiting amount of imiquimod, wherein the imiquimod is administered intralesionally by injection or infusion in combination with a pharmaceutically acceptable carrier, the imiquimod is administered as particles in a particulate suspension and in sufficient quantities to provide continuous release of imiquimod, and the neoplastic tumors and lesions comprise basal cell carcinoma.

2. The method of claim 1 wherein the imiquimod is administered to a human patient having a neoplastic tumor or lesion in an amount which is effective to inhibit the growth of the tumor or lesion.

3. The method of claim 1 wherein the imiquimod is crystalline in form.

4. The method of claim 1 wherein the imiquimod is amorphous in form.

5. The method of claim 1 further comprising adjusting the size of the imiquimod particles in the particulate suspension to control the dissolution of the particular suspension.

6. The method of claim 1 wherein the pharmaceutically acceptable carrier comprises a sterile solution of saline.

7. The method of claim 6 wherein saline is present in an amount of approximately 0.9% w/v.

8. The method of claim 6 wherein the pharmaceutically acceptable carrier comprises one of more of the following agents: hydroxypropylcellulose, polyethylene glycol, and polysorbate.

9. The method of claim 1 wherein the administering does not induce side effects resulting from systemic cytokine stimulation including nausea, fever, or flu-like symptoms.

10. The method of claim 1 wherein the imiquimod is administered in a single injection.

11. A method of inhibiting growth of neoplastic tumors and lesions, the method comprising administering to a mammal in need thereof a therapeutically effective, growth-inhibiting amount of imiquimod, wherein the imiquimod is administered intralesionally by injection or infusion in combination with a pharmaceutically acceptable carrier, the imiquimod is administered as particles in a particulate suspension and in sufficient quantities to provide continuous release of imiquimod, the administering induces cytokine stimulation in the neoplastic tumor or lesion without inducing side effects resulting from systemic imiquimod exposure, and the neoplastic tumors and lesions comprise basal cell carcinoma.

12. The method of claim 11 wherein the imiquimod is administered in a single injection.

13. A method of inhibiting growth of neoplastic tumors and lesions, the method comprising administering to a mammal in need thereof a therapeutically effective, growth-inhibiting amount of imiquimod, wherein the imiquimod is administered intralesionally by injection or infusion in combination with a pharmaceutically acceptable carrier, wherein the imiquimod is administered as particles in a particulate suspension and in sufficient quantities to provide continuous release of imiquimod, wherein the particles are in an amorphous form or a crystalline form, the administering induces cytokine stimulation in the neoplastic tumor or lesion without inducing nausea, fever, or flu-like symptoms resulting from systemic imiquimod exposure, and the neoplastic tumors and lesions comprise basal cell carcinoma.

* * * * *